United States Patent
Buchholz et al.

(10) Patent No.: US 9,566,561 B2
(45) Date of Patent: Feb. 14, 2017

(54) REACTOR HAVING ELECTROLUMINESCENT PARTICLES IN THE REACTION MEDIUM

(71) Applicants: Friedrich-Alexander-Universitaet Erlangen-Kuernberg, Erlangen (DE); Rainer Buchholz, Hessdorf (DE)

(72) Inventors: Rainer Buchholz, Hessdorf (DE); Christoph Lindenberger, Busan (KR); Paul Manstetten, Kareth (DE); Martin Heining, Erlangen (DE)

(73) Assignees: FRIEDRICH-ALEXANDER-UNIVERSITAET ERLANGE, Erlangen (DE); Rainer Buchholz, Hessdorf (DE)

( * ) Notice: Subject to any disclaimer, the term of this patent is extended or adjusted under 35 U.S.C. 154(b) by 0 days.

(21) Appl. No.: 14/434,605

(22) PCT Filed: Oct. 11, 2013

(86) PCT No.: PCT/EP2013/003056
§ 371 (c)(1),
(2) Date: Apr. 9, 2015

(87) PCT Pub. No.: WO2014/056617
PCT Pub. Date: Apr. 17, 2014

(65) Prior Publication Data
US 2015/0251152 A1    Sep. 10, 2015

(30) Foreign Application Priority Data
Oct. 11, 2012    (EP) ..................................... 12007117

(51) Int. Cl.
C12M 1/42    (2006.01)
B01J 19/08    (2006.01)
(Continued)

(52) U.S. Cl.
CPC ............. B01J 19/087 (2013.01); C12M 21/02 (2013.01); C12M 31/10 (2013.01); C12M 35/02 (2013.01); C12N 1/12 (2013.01); B01J 2219/085 (2013.01)

(58) Field of Classification Search
CPC .................................. C12M 1/42; C12M 1/002
See application file for complete search history.

(56) References Cited

U.S. PATENT DOCUMENTS

2011/0281295 A1* 11/2011 Sylvestre ............... C12M 21/02
435/29

FOREIGN PATENT DOCUMENTS

DE        19747994 C1    1/1999
DE    102007055569 A1    5/2009
(Continued)

OTHER PUBLICATIONS

J. Kuipers et al., "Near field resonant inductive coupling to power electronic devices dispersed in water", Sensors and Actuators A178 (2012) 217-222 (6 pages total).
(Continued)

*Primary Examiner* — Rosanne Kosson

(57) ABSTRACT

The invention teaches the use of particles (7) capable of light emission in chemical, biochemical, and/or biological reactors (1), wherein the reactor (1) comprises at least one emission element (4) for emitting electromagnetic alternating fields in a reaction chamber (5) of the reactor (1), wherein the particles (7) capable of light emission are suspended in a fluid reaction medium present in the reaction chamber (5), wherein the reaction medium contains photoreactants (6), and wherein the particles (7) capable of light emission are excited by means of supply of energy to the
(Continued)

emission element (4), in a wireless manner, to emit light that activates the photoreactants (6), a photoreactor (1) and the uses thereof.

3 Claims, 3 Drawing Sheets

(51) Int. Cl.
*C12M 1/00* (2006.01)
*C12N 1/12* (2006.01)

(56) References Cited

FOREIGN PATENT DOCUMENTS

| | | |
|---|---|---|
| DE | 102009015925 A1 | 10/2010 |
| DE | 102010007168 A1 | 8/2011 |
| EP | 0817537 A1 | 1/1998 |
| EP | 1088874 A1 | 4/2001 |
| EP | 1326959 A1 | 7/2003 |
| WO | 2005/005326 A1 | 1/2005 |
| WO | 2008151376 A1 | 12/2008 |
| WO | 2009043763 A1 | 4/2009 |
| WO | 2010/129278 A1 | 11/2010 |

OTHER PUBLICATIONS

International Preliminary Report on Patentability and Written Opinion issued Apr. 14, 2015 in connection with corresponding International Application No. PCT/EP2013/003056 (16 pages total).
Search report of 200908498, WO, A3, Feb. 5, 2009, Bionavitas Inc.

\* cited by examiner

REACTOR HAVING ELECTROLUMINESCENT PARTICLES IN THE REACTION MEDIUM

FIELD OF THE INVENTION

The invention concerns a novel use of particles capable of light emission, a photoreactor comprising a reaction chamber, in which a fluid reaction medium is contained, uses of such a photoreactor, and methods for cultivating phototrophous cells and for carrying-out photoreactions.

BACKGROUND OF THE INVENTION AND PRIOR ART

Photobioreactors are a special field in the area of bioengineering, since the reactors therefor are not reactors being only adapted also for the area of chemical process engineering, wherein the optimization of the reaction procedures only comprises the transportation processes and mixing techniques. Rather, for photoreactors, the input of light and the distribution thereof within the reaction medium plays an important role, the more so as light is not dispersible in aqueous media, at least not now. Up to today, this technical challenge led to various designs for photobioreactors.

In principle, stirred-tank reactors (often with internal illumination), tubular reactors, (vertical) column reactors, and flat-plate reactors can be distinguished. Generally, the supply of light energy to the reaction medium occurs from outside, i.e. through a reactor wall being transparent for light. Reactors with such external supply of light can only difficultly be extended from a laboratory scale to an industrial scale, since the efficiency of the supply of light and thus of the photobioreactions depends on the surface of the transparent reactor wall and will thus not increase linearly with an enlargement of the reactor volume. An enlargement of the reactor volume will thus lead to decreasing reaction rates.

Another problem of such externally lighted photobioreactors is that the light conditions within the reaction medium, which contains turbid matter, together with the cells, are inhomogeneous, and this inhomogeneity will even increase with increasing cell density, i.e. with the progress of the reaction. Therefore, the mixing behavior in such photobioreactors also plays a very important role. In principle, it would be desirable to arrange for substantially identical reaction conditions within different volume units of the reaction medium.

Finally, the supplied light power cannot be increased infinitely, since in many phototrophous microorganisms a photoinhibition will occur as from a certain light intensity. This is consequently the maximum value in an arbitrary volume element of the reactor space, and in other volume elements the light power is then clearly lower, due to absorption, with the consequence of a lower photobiosynthesis performance.

A design known from the practice is a stirred-tank reactor, into the reaction chamber of which optical fibers are guided, which are supplied with light from outside. The light is guided through the optical fibers into the reaction medium and is emitted there. With a suitable arrangement of the ends of the optical fibers in the reaction chamber, a nearly homogeneous illumination of the reaction medium can be achieved. However, the optical fibers will disturb the mass transportation processes, convection and diffusion, for geometric reasons to a substantial degree, thereby then in turn the homogeneity of the distribution of the reactants within the reaction chamber being adversely affected, and thus ultimately the achievable reaction rates. An example of such a type of reactor is described in the document DE 10 2007 055 569 A1.

Another class of photobioreactors are the flat-plate reactors. Just as an example, reference is made to the document DE 10 2009 015 925 A1. A characteristic parameter of this design is the thickness of the at least one-side transparent reactors, which typically is in the range of 70 mm. They are operated analogously to so-called "airlift" reactors with an exposure to gas along the reactor bottom. This permits a mixing behavior, which with an optimum height and length of the reactor will come close to 80% of the mixing efficiency of an ideal stirred tank. Nevertheless, the mass transfer of $CO_2$ and $O_2$ is not very efficient due to the short lifetime of gas bubbles. This can be improved by different parameters, whereby a scale-up up to 133 l becomes possible (see document EP 1 326 959 B1).

In principle, tubular reactors in biotechnology have the same disadvantages as in chemical process engineering. The biggest disadvantage with horizontal tubular reactors is that the reduction of substrate along the flow direction of the reaction medium, thus consequently the reaction rates being reduced, can be neglected for short tubes, since then the reaction or growth kinetics is in a first approximation of zero order. However, this describes only the main reaction of the process, for instance the chemical properties of $CO_2$ in water can substantially affect the pH value, thus the growth being inhibited or slowed down. Further, the necessary removal of $O_2$ from the reaction medium plays a role influencing the growth. All these problems are strongly increasing with increasing tube length. Nevertheless, such photobioreactors of up 500 km length and a photo-active volume of 600 m3 are known in the art. The reaction efficiency is however comparatively poor for the mentioned reasons and for an up-scale, the length increase and thus the technical efforts need to be increased in a disproportionate manner.

Another type of tubular reactor is formed by a vertical arrangement of the tubes, with the tubes being U-shaped and having in the range of the U-curve a gassing device. Thereby, further the mass transfer through the U-legs is caused. For an example of such a type of reactor in biotechnology, reference is made to the document DE 197 47 994 C1. With such type of reactor, a scale-up up to 120 l is possible, but there is still a necessity of some improvement.

With regard to mixing behavior and mass transfer, a stirred-tank reactor would be ideal. Such stirred-tank reactors with transparent walls and external lighting are up to now used as photobioreactors on a laboratory scale only and not on an industrial scale, due to the problems of the homogeneous introduction of the light into all volume elements of the reaction chamber. The attenuation of the light follows an exponential law with the distance from the transparent reactor wall, the more so as also the extinction coefficient increases with increasing cell density. For a scale-up, therefore, it is basically always tried to increase the ration of (transparent) surface to volume, or to optimize it. In a not-turbid liquid, the light intensity of a cylindrical body lighted from all around would lead to an increased intensity in the center axis, similar to the effect of a condenser lens. In a cell suspension, then a cell density can be established, in which there is approximately everywhere in the cross section the same light intensity. This cell density is however not optimal in view of the achievable production performance. In principle, the above problems do not only exist in the field of the photobioreactors, but also in the field of the chemical reactors for photoreactions of chemical reactants.

SUMMARY OF THE INVENTION

Technical object of the invention.

It is the technical object of the invention to provide a reactor assembly for photoreactions, i.e. photobioreactions or chemical photoreactions, which assures a practically homogeneous illumination of the reaction chamber, without obstructing or otherwise adversely affecting the mass transfer by disturbing components in the reaction chamber.

DETAILED DESCRIPTION OF THE INVENTION

Basics of the invention and preferred embodiments.

For achieving this technical object, the invention teaches the use of particles capable of light emission in chemical, biochemical, and/or biological reactors, wherein the reactor comprises at least one emission element for emitting electromagnetic alternating fields in a reaction chamber of the reactor, wherein the particles capable of light emission are incorporated in a fluid reaction medium present in the reaction chamber, wherein the reaction medium contains photoreactants, and wherein the particles capable of light emission are excited by means of supply of energy to the emission element in a wireless manner (without a line connection between particles and energy source) to emit light that activates the photoreactants.

In other words, the particles capable of light emission are suspended in the reaction medium and are wirelessly enabled for light emission by an emission element. Thereby that the particle are distributed in the reaction medium and circulate therein together with the other components of the reaction medium, a nearly homogeneous illumination of the reaction chamber occurs, and that without the particles adversely affecting the mass transfer within the reaction chamber optimized with usual measures for the respective reaction. All ratios surface to volume of the reaction chamber become irrelevant and a scale-up with proportionally increasing product formation is possible without problems. Surprisingly, it was found with respect to phototrophous cells or microorganisms that even high-energy electric and/or magnetic alternating fields do not measurably affect the growth in the frequency ranges explained further below.

In principle, the reaction medium may be liquid or substantially gaseous, for instance an aerosol. Preferably, it is a liquid, aqueous and/or organic, while for photobioreactions aqueous reaction media are adequate.

The photoreactants may be living phototrophous cells or organisms, in particular aquatic microorganisms, preferably micro-algae or cyanobacteria, or may comprise at least one chemical substance, which can be brought by absorption of light into an excited singlet or triplet state and releases the received energy by a chemical reaction with other reactants present in the reaction medium.

Typical phototrophous cells and/or microorganisms, the cultivation of which on an industrial scale would be desirable, include: Cyanophyta (e.g., *Arthrospira platensis, Lyngbya taylorii* and *Nostoc ellipsosporum*), Chlorophyta (e.g., *Chlorella vulgaris, Haematococcus pluvialis, Dunaliella salina, Chlamydomonas reinhardtii*), Rhodophyta (e.g., *Porphyridium purpureum*), Heterokontophyta (e.g., *Ochromonas danica*), Haptophyta (e.g., *Isochrysis galbana*), Dinophyta (e.g., *Amphidinium carterae*). These may by cells or microorganisms, which themselves represent the sought product, but also cells or microorganisms, which form or express a sought product. In any case, typically, energy supplying substances are continuously or discontinuously added to the reaction medium, and the composition, kind, or addition and dosage means of said substances can easily be selected by the man skilled in the art under consideration of the respective type of cell or microorganism. If cells or microorganisms to be cultivated form substances, which inhibit the cell growth or a product expression, it may be provided that such substances are continuously or discontinuously removed. This may for instance occur by immobilized substance-specific absorption or reaction agents contacted with the reaction medium or by permeation membranes selected according to substances to be separated. When the cells or microorganisms themselves are the product, then part of the population in the reaction medium is continuously or discontinuously separated in a conventional manner. In principle, all conventional technologies of bioreactors can be employed.

Typical chemical photoreactions on an industrial scale are for instance: photocatalytic water splitting for obtaining hydrogen, photochemical water and waste water treatment by means of water photolysis, photolysis of hydrogen peroxide, photolysis of ozone, photocatalysis with titanium dioxide ($TiO2$), photo-Fenton type process. Here, too, the supply of educts and the discharge of products can occur in a conventional manner and under consideration of the respective reaction.

As particles capable of light emission are contemplated all constructs, which are chemically and physically stable in the reaction medium to be used. If necessary, the particles may comprise an envelope being transparent for the light emitted by the particles, which envelope is chemically inert with respect to the reaction medium or the components thereof.

The particles capable of light emission may include at least one LED component and at least one antenna element electrically connected with the LED component for receiving incident electromagnetic alternating fields and converting the received alternating fields into electric energy. LED components are commercially available electronic components with different emission colors. The color suitable for a certain photobioreaction or chemical photoreaction can easily be selected by the person skilled in the art, it results from the desired photoreaction. Further, suitable antenna elements are for instance coils, either commercially available or made from wire or as a printed or integrated circuit. Dimensioning of the antenna element appropriately is made according to the frequency of the electric alternating field that is to be irradiated and the electric power required by the LED component. It is also possible to connect, between the antenna element and the LED component, a storage for electric energy and, if applicable, an electronic circuitry for a constant supply of electric energy from the storage to the LED component. Thereby, the light emission is held constant with varying reception of electric energy by the antenna element. Such particles suitably have an envelope or a housing of a transparent material being inert in the reaction medium under reaction conditions. This material should of course be permeable for electric alternating fields.

Alternatively, the LED component can be replaced by any material/component, which is capable of emitting light from electric current and/or electric alternating fields (e.g., incandescent filament lamp, OLED, electroluminescence emitter, etc.).

Basically, the emission element for emitting electromagnetic alternating fields may be arbitrary, i.e. an inductive and/or capacitive emitter. It may be located outside a wall of the reactor, preferably at the outside resting against the wall, at the inside resting against the reactor wall, or spaced to the reactor wall in the reaction chamber. In the first case, the reactor wall should be permeable to the electric and/or magnetic alternating field, or should not be attenuating the same and consequently be made from a corresponding material. As reactor walls are typically contemplated glass materials and organic polymeric materials, which are selected in a conventional manner. When a coil is provided as an inductive emission element at the inside in connection with a metallic material of the reactor wall, it may be recommended to line the reactor space or the reactor wall at the inside with a material having a high magnetic permeability, for instance mu-metal, in order that no disturbing eddy currents are induced in the metallic reactor wall. When the coil is located at the outside of the reactor wall, it may be recommended to dispose, again at the outside of the coil, a shield covering the coil at the outside, which is made from a material of high magnetic permeability, for instance mu-metal.

Concerning for instance the specific dimensioning of the components of the invention, in particular of the emission element and the antenna element in the embodiment with an LED component, reference is made to the document J. Kuipers et al., Sensors and Actuators A178 (2012) 217-222. In the case of coils as antenna elements in the embodiment with an LED component, it is also recommended that the coil is formed of partial coils, the coil axes of which show in different spatial directions, in particular three spatial directions, since then an optimal energy reception irrespective of the orientation of the particle in the reaction medium is assured.

As excitation frequencies of the electric and/or inductive alternating fields, a range from 1 kHz to 1 MHz, in particular from 20 kHz to 500 kHz, for instance from 100 kHz to 200 kHz is contemplated. The alternating field may also be pulsed ("on"/"off"), with pulse frequencies in the range from 10–5 Hz to 1 kHz. The duty cycle ("on" to "off") of these pulses may be in the range from 1:20 to 10:1.

It is particularly advantageous, though not necessary, when the particles are provided with a mean density that differs by less than 10%, preferably less than 5%, in particular less than 2%, from the density of the reaction medium under reaction conditions. Then the particles are capable of so to speak floating in the reaction medium, and due to the resulting relatively homogeneous distribution of the particles, a homogeneous light emission in the reaction medium will also be obtained. When the mean density of the particles, however, is distinctly different from that of the reaction medium, then, nevertheless, a relatively homogeneous distribution of the particles, though not quite so optimal, can be achieved by agitation of the reaction medium.

The invention further concerns in another aspect a photoreactor comprising a reaction chamber, in which a fluid reaction medium is contained, wherein the reactor medium comprises particles capable of light emission and photoreactants, wherein the reactor comprises at least one emission element for emitting electromagnetic alternating fields in the reaction chamber of the reactor, wherein the emission element is connected to an energy source, and wherein the particles capable of light emission can be excited by means of supply of energy to the emission element to emit light that activates the photoreactants.

Another aspect of the invention concerns the use of a photoreactor according to the invention for carrying-out photoreactions, in particular for cultivating phototrophous cells or organisms, in particular aquatic microorganisms, preferably micro-algae or cyanobacteria, or for carrying-out chemical photoreactions, wherein the photoreactants comprise at least one chemical substance, which can be brought by absorption of light into an excited singlet or triplet state and releases the received energy by a chemical reaction with other reactants in the reaction medium.

Again another aspect of the invention teaches a method for cultivating phototrophous cells or organisms, in particular aquatic microorganisms, preferably, micro-algae or cyanobacteria, wherein these cells or organisms are cultivated, in particular circulated, in a reaction medium of a photoreactor according to the invention under supply of energy to the emission element for a given time and under given reaction conditions.

Another aspect of the invention teaches a method for carrying-out chemical photoreactions, wherein the photoreactants comprise at least one chemical substance, which can be brought by absorption of light into an excited singlet or triplet state and releases the received energy by a chemical reaction with other reactants in the reaction medium, wherein these reactants are reacted in a reaction medium of a photoreactor according to the invention under supply of energy to the emission element for a given time and under given reaction conditions.

The explanations given for the first aspect of the invention apply in an analogous manner for the other aspects of the invention, too. The teaching of the invention can in principle be used for all types of reactors, for stirred-tank reactors, flat-plate reactors, and tubular reactors.

BRIEF DESCRIPTION OF THE DRAWINGS

In the following, the invention is explained in more detail with reference to figures representing examples of execution only. There are:

FIG. 3(a) shows the tubular reactor with a coil at the outside of the reactor wall and FIG. 3(b) shows the tubular reactor at the inside of the reactor wall.

EXAMPLE 1

Flat-Plate Reactor According to the Invention

Figure 1:
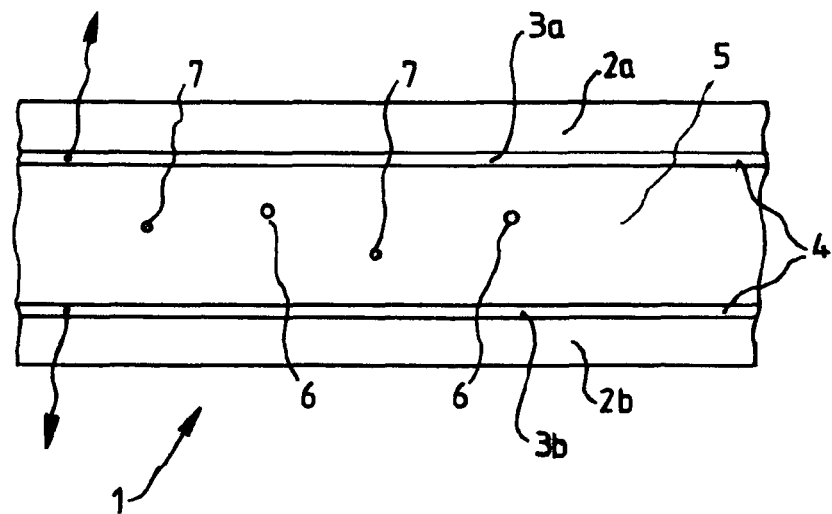
FIG. 1: a diagrammatic representation of a flat-plate reactor with particles capable of light emission and capacitive excitation.
Figure 5:
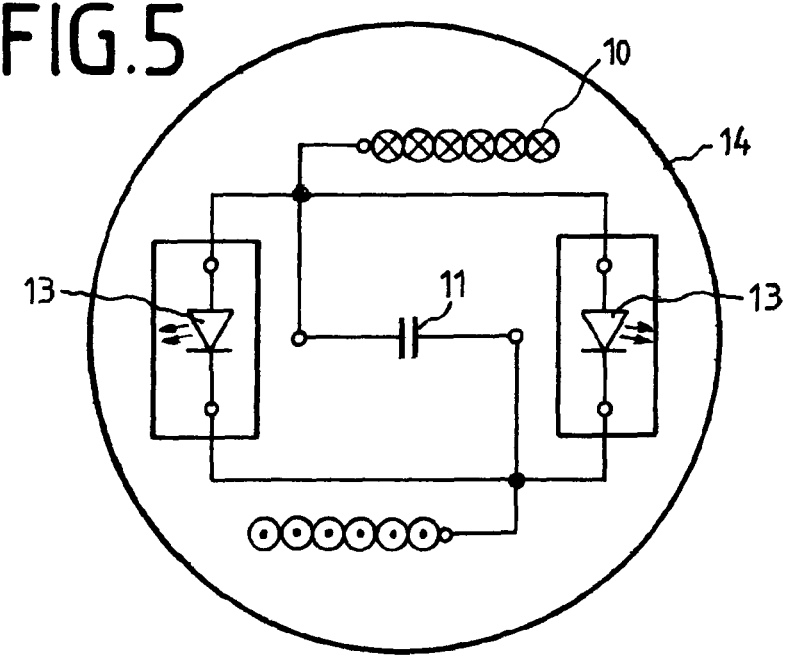
FIG. 5: a diagrammatic representation of the overall structure of a particle with LED.
Figure 6:
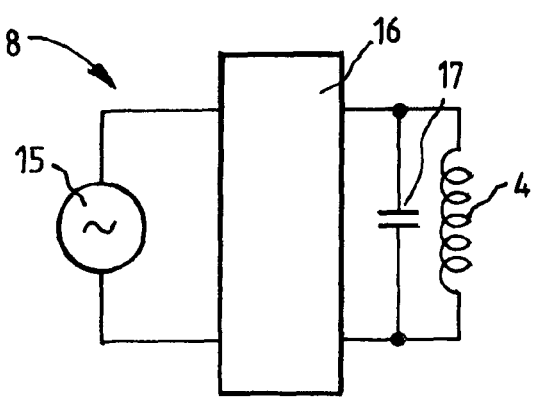
FIG. 6: a diagrammatic representation of a generator circuitry for inductive and/or capacitive excitation.

In FIG. 1 can be seen a flat-plate reactor 1 in a cross section vertically to the main faces. Two opposite reactor walls 2a,b in a distance of 70 mm can be seen. On the inside of the reactor walls 2a,b, two surface electrodes 3a,b made from an electrically conductive material are disposed, which are electrically isolated from the reaction medium by a suitable non-conductive coating. The two surface electrodes 3a,b form a capacitor 4 as an emission element 4 of a generator circuitry 8, as shown in FIG. 6. Between the reactor walls 2a,b is disposed the reaction chamber 5. The latter is filled with a reaction medium, in which, on the one hand, microorganisms 6 as photoreactants 6 and, on the other hand, particles according to FIG. 5 are present. Means for transportation of the reaction medium or the mixture thereof are not shown for clarity reasons.

When the generator circuitry 8 is activated, electric alternating fields are emitted by the surface electrodes 3a,b in the reaction chamber 5, which fields excite the floating particles 7 to light emission.

EXAMPLE 2

Stirred-Tank Reactor According to the Invention

Figure 2:
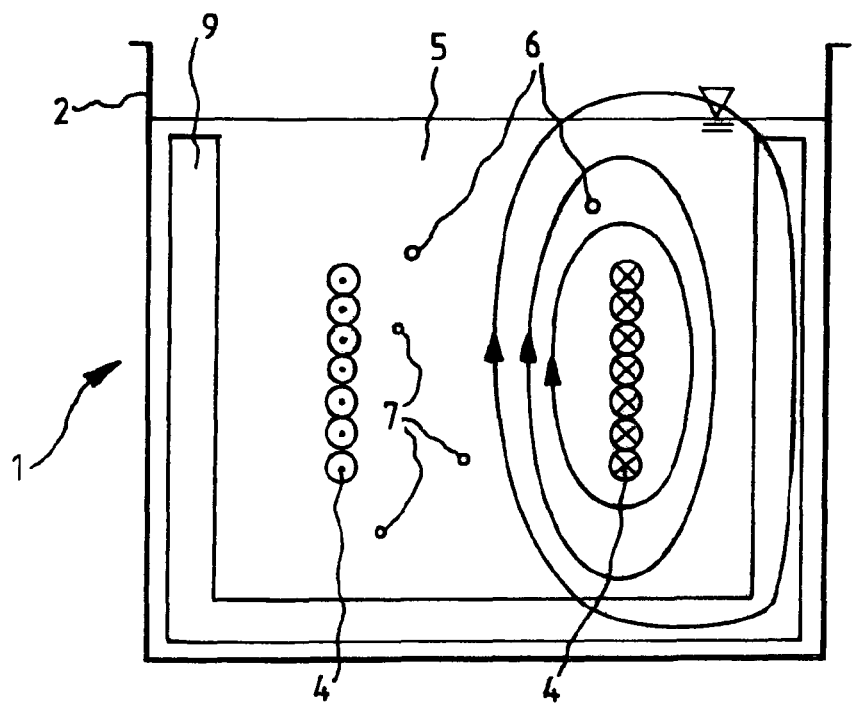
FIG. 2: a diagrammatic representation of a stirred-tank reactor with particles with LED components and inductive excitation.

In FIG. 2 can be seen a stirred-tank reactor 1 in a cross section. The reactor wall 2 forming the tank can be seen. On the inside of the reactor wall 2 is disposed a coil 4 as an emission element 4 of a generator circuitry 8, as shown in FIG. 6. Within the reactor wall 2, the reaction chamber 5 is disposed. The latter is filled with a reaction medium, in which on the one hand, microorganisms 6 as photoreactants 6 and, on the other hand, LED particles 7 from FIG. 5 are suspended. Means for transportation of the reaction medium or the mixture thereof are not shown for clarity reasons. Outside or inside the reactor wall 2, a shield 9 may be provided.

When the generator circuitry 8 is activated, electric alternating fields are emitted by the coil 4 in the reaction chamber 5, which fields excite the floating particles 7 to light emission.

EXAMPLE 3

Tubular Reactor According to the Invention

Figure 3A:
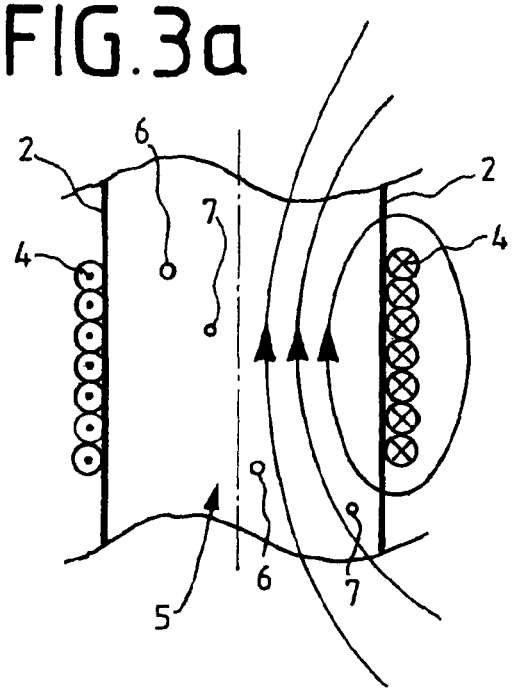
FIGS. 3a and 3b: diagrammatic representation of a tubular reactor.

In FIG. 3a can be seen a tubular reactor 1 in a cross section. The reactor wall 2 forming a tube can be seen. Outside the reactor wall 2 is disposed a coil 4 as an emission element 4 of a generator circuitry 8, as shown in FIG. 6. Inside the reactor wall 2 is disposed the reaction chamber 5. The latter is filled with a reaction medium, in which on the one hand, microorganisms 6 as photoreactants 6 and, on the other hand, LED particles 7 from FIG. 5 are suspended. Means for transportation of the reaction medium or the mixture thereof are not shown for clarity reasons.

When the generator circuitry 8 is activated, electric alternating fields are emitted by the coil 4 in the reaction chamber 5, which fields excite the floating particles 7 to light emission.

Figure 3B:
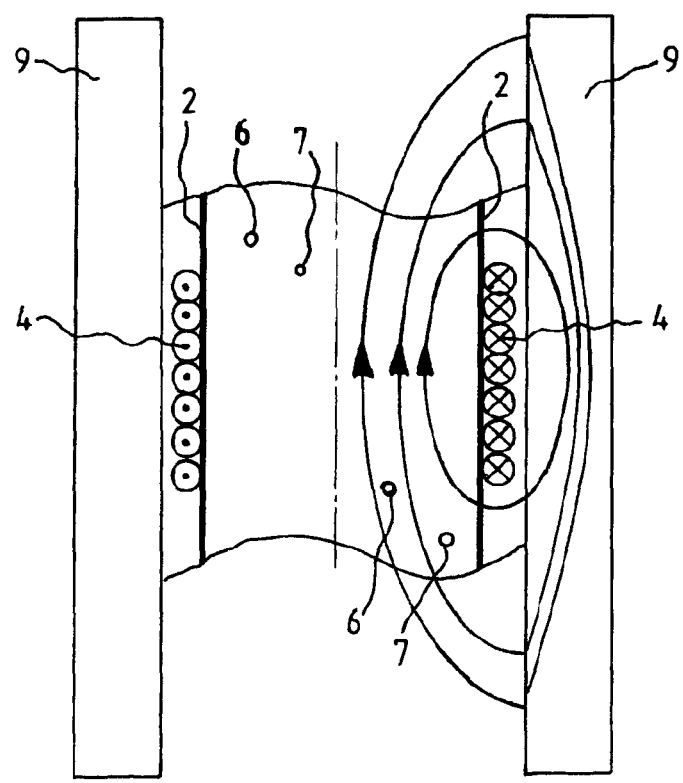

In FIG. 3b is disposed, outside the coil 4 and comprising the latter, a shield 9 made from a magnetically highly permeable material, such as mu-metal. From a comparative inspection of FIGS. 3a and 3b, the influence of the shield 9 on the magnetic field lines can be seen.

EXAMPLE 4

LED Particles

Figure 4:
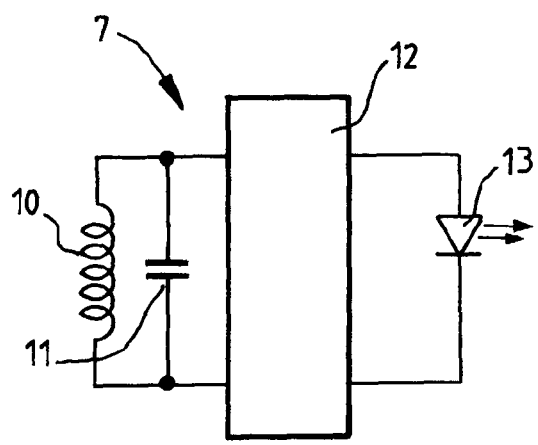
FIG. 4: a diagrammatic circuit of a particle with LED.

In FIG. 4 can be seen a diagrammatic circuit of an LED particle 7. It comprises a coil 10 acting as an antenna element 10, and a capacitor 11, forming a resonant circuit. Connected thereto is an energy storage and charge control unit 12. Connected thereto in turn is the LED 13.

In FIG. 5, again, can be seen a coil 10, a capacitor 11, and, in this example, two LEDs 13. Of course, here too, an energy storage and charge control unit 12 may be provided. The circuitry is enclosed by an envelope 14 made from a plastic material being inert in the reaction medium, or may be cast therein.

EXAMPLE 5

Generator Circuitry

In FIG. 6 can be seen a generator circuitry 8 comprising an oscillator 15, an amplifier 16, a coil 4 acting as an emission element 4, and a capacitor 17. Alternatively to the representation of FIG. 6, coil 4 and capacitor 17 may also be connected in series.

The invention claimed is:
1. A method for cultivating phototrophic cells or microorganisms, comprising the step of cultivating the cells or microorganisms in a reaction medium of a photobioreactor under supply of energy to the emission element for a given time,
   wherein the photobioreactor comprises
   (a) a reaction chamber, in which a fluid reaction medium is contained therein, wherein the reaction medium includes
   (b) particles capable of light emission and (c) phototrophic cells or microorganisms, wherein the photobioreactor comprises
   (d) at least one emission element to emit electromagnetic alternating fields in the reaction chamber of the reactor, which emission element is connected to an energy source, and wherein the particles capable of light emission can be excited by electromagnetic energy from the emission element, in a wireless manner, to emit light that activates the phototrophic cells or microorganisms.
2. The method of claim 1, wherein the phototrophic cells or microorganisms are aquatic cells or microorganisms.
3. The method of claim 1, wherein the phototrophic cells or microorganisms are microalgae or cyanobacteria.

* * * * *